United States Patent [19]

Davis

[11] Patent Number: 4,919,811

[45] Date of Patent: Apr. 24, 1990

[54] AFFINITY MEMBRANES HAVING PENDANT HYDROXY GROUPS AND PROCESSES FOR THE PREPARATION AND USE THEREOF

[75] Inventor: James C. Davis, Hudson, Ohio

[73] Assignee: The Standard Oil Company, Cleveland, Ohio

[21] Appl. No.: 144,312

[22] Filed: Jan. 14, 1988

[51] Int. Cl.$^5$ .............................................. B01D 13/00
[52] U.S. Cl. ........................ 210/500.36; 210/500.41; 562/544
[58] Field of Search ................... 562/544; 210/500.41, 210/500.33, 500.36, 500.27, 500, 21, 500.1

[56] References Cited

U.S. PATENT DOCUMENTS

| | | | |
|---|---|---|---|
| 3,351,495 | 11/1967 | Larsen et al. | 136/146 |
| 3,770,631 | 11/1973 | Fekete et al. | 210/53 |
| 3,880,989 | 4/1975 | Garcia | 424/11 |
| 4,000,121 | 12/1976 | Garcia | 260/112 B |
| 4,046,843 | 9/1977 | Sano et al. | 264/22 |
| 4,143,218 | 3/1979 | Adams et al. | 429/254 |
| 4,163,714 | 8/1979 | Gregor | 210/23 F |
| 4,377,481 | 3/1983 | Jakabhazy | 210/500.2 |
| 4,525,374 | 6/1985 | Vaillancourt | 427/2 |
| 4,596,660 | 6/1986 | Hou | 210/692 |
| 4,754,089 | 6/1988 | Matson et al. | 562/544 |

OTHER PUBLICATIONS

"Affinity Binding, an Evolving Technology", The 1986 Fourth Annual Membrane Technology/Planning Conference, Nov. 5-7, 1986, Randall H. Morse.

*Primary Examiner*—Frank Sever
*Attorney, Agent, or Firm*—Larry W. Evans; Joseph G. Curatolo; Sue E. Phillips

[57] ABSTRACT

Polymeric affinity membranes comprise a precursor filtration membrane and a plurality of reaction sites provided on the surface of the membrane selective to binding a specific biological material. A process for the preparation of such affinity membranes includes the steps of providing a copolymer compatible with a water insoluble polymer matrix and having a plurality of hydroxyl groups, activating the hydroxyl groups and a compound selected from the group consisting of organic compounds reactive with a hydroxyl group in the presence of water miscible solvent to provide a derivatized copolymer containing active adducts, forming a solution of the derivatized copolymer and the polymer matrix to form a polymer blend solution, casting the polymer blend solution and, quenching the cast polymer blend solution in water. A process for selectively removing biological materials from fluids includes the step of passing the fluids over an affinity membrane which comprises a precursor filtration membrane and a plurality of reaction sites provided on the surface of the membrane selective to binding a specific biological material.

6 Claims, No Drawings

AFFINITY MEMBRANES HAVING PENDANT HYDROXY GROUPS AND PROCESSES FOR THE PREPARATION AND USE THEREOF

TECHNICAL FIELD

The subject invention relates to and improves upon filtration membranes which have been developed for protein purification where low protein binding hasbeen achieved via the use of block copolymers of polyethylene oxide and propylene oxide. When protein becomes irreversible bound to existing filtration membranes, a decline in flux results. This invention employs polyethersulfones as the polymer matrix, known materials which possess the requisite mechanical strength and chemical resistivity for a membrane but which, by themselves, are hydrophobic and therefore, readily fouled by proteins. In related work, the polymer matrix has been modified with the foregoing copolymers, resulting in the introduction of fouling resistant characteristics.

These polymer blend or precursor membranes have been further modified, according to the present invention, and provide a specific binding capacity for a given protein or other biological molecule. The membranes are thus employed in a first process for binding specific biological materials. By the addition of a first biological member, e.g., an antigen, the membrane will then have a further affinity for a corresponding antibody in a second process of the present invention.

BACKGROUND ART

Affinity membranes are becoming widely accepted for use in immunoaffinity binding tests such as the Western Blot and Southern Blot techniques. This is the type of assay currently used for AIDS, Hepatitis B, and other virulent blood disease testing. Details of the technology of affinity binding have been summarized in a paper entitled "AFFINITY BINDING An Evolving Technology" presented at the 1984 Fourth Annual Membrane Technology/Planning Conference by Randall H. Morse.

Known polymer membranes possess mechanical strength and chemical resistance but lack hydrophilicity and passivity to proteins. Thus, the membrane is quickly fouled by adsorption of proteins or other biological materials. Methods for the modification of the membranes have involved chemical modification of the polysulfone aromatic ring by sulfonation, chloromethylation, nitration and Friedel-Crafts reaction; grafting a hydrophilic material onto a pre-formed film support; plasma polymerization of nitrogen-containing compounds directly onto porous polysulfone and blending of a hydrophilic, compatible additive such as polyvinylpyrrolidone with the polysulfone.

More specifically, the blending of polymers is known for altering the hydrophilic-hydrophobic balance of a membrane system. Inasmuch as most polymers are thermodynamically incompatible, polymer blending has heretofore found limited utility. The choices of appropriate polymers for the formation of compatible blends are limited to species where significant interation can occur. Several recent patents have provided semipermeable membranes, ultrafiltration membranes and the like and processes for their preparation which involve mixing or blending of polymers.

U.S. Pat. No. 4,046,843 provides a process for preparing semipermeable membranes from one of several mixtures. One is a water-insoluble high polymer (polysulfone) and a water-soluble high polymer (polyethylene oxide). Another is a water insoluble high polymer (polysulfone) and a water soluble surfactant including anionic (sodium laurylsulfate), nonionic (polyoxyethylene lauryl ether) and natural surfactants (saponin). The membrane is formed by casting a solution of a foregoing mixture, exposing the formed article to a plasma for crosslinking and then washing the exposed article with water for removal of uncrosslinked water-soluble polymer or water-soluble surfactant.

U.S. Pat. No. 4,377,481 is directed toward blended polymeric membranes which comprise a water-insoluble matrix polymer and a water-insoluble copolymer. The latter comprises an acrylate or methacrylate monomer, the homopolymer of which is water-insoluble and matrix compatible while the second monomer contains cationic or anionic groups and which if homopolymerized would be water-soluble but matrix incompatible.

Despite the widespread existence of different processes for the extraction of proteins from fluids; the known filtration membranes and related processes and, the various techniques for modifying polymer membranes, the art has not recognized heretofore a process for the preparation of affinity membranes involving the modification of polymer blends to impart selective protein binding. As a result of the present invention nonfouling, affinity membranes have been obtained.

SUMMARY OF THE INVENTION

It is therefore an object of the present invention to provide affinity membranes which provide a limited number of active sites available to bind specific proteins and other biological materials.

It is another object of the present invention to provide affinity membranes that will bind with a first biological material having a binding capacity for a second biological material.

It is a further object of the present invention to provide a process for the preparation of an affinity membrane from precursor membranes carrying hydroxyl groups.

It is yet another object of the present invention to provide a process for the preparation of an affinity membrane carrying a first biological material.

It is a further object of the present invention to provide processes for the separation and removal of first and second biological materials from fluids using the foregoing affinity membranes.

In general, a polymeric affinity membrane according to the present invention comprises a precursor filtration membrane and a plurality of reaction sites provided on the surface of the membrane selective to binding a specific biological material.

A process for the preparation of affinity membranes comprises the steps of providing a copolymer compatible with a water insoluble polymer matrix and having a plurality of hydroxyl groups, activating the hydroxyl groups with a compound selected from the group consisting of organic compounds reactive with a hydroxyl group in the presence of a water miscible solvent to provide a derivatized copolymer containing active adducts, forming a solution of the derivatized copolymer and the polymer matrix to form a polymer blend solution, casting the polymer blend solution and, quenching the cast polymer blend solution in water.

A second process for the preparation of affinity membranes comprises the steps of providing a precursor membrane having a plurality of hydroxyl groups and activating the hydroxyl groups with a compound selected from the group consisting of organic compounds reactive with a hydroxyl group to provide a derivatized affinity membrane containing active adducts.

A process for selectively removing biological materials from fluids comprises the step of passing the fluids over an affinity membrane which comprises a precursor filtration membrane and a plurality of reaction sites provided on the surface of the membrane selective to binding a specific biological material. The process can also employ the membrane and bound biological material to remove a second biological material to which the first bound material has an affinity.

These and other objects of the present invention together with the advantages thereof over existing filtration membranes and processes for the preparation and use, which shall become apparent from the specification which follows, are accomplished by the invention as hereinafter described and claimed.

PREFERRED MODE FOR CARRYING OUT THE INVENTION

The affinity membranes of the present invention are capable of filtering particles falling between about 500 millimicrons to 10 microns. These ranges coincide with particles that are filterable with ultrafiltration membranes as well as with microfilters and hence, the present membranes have not been designated as either type. With the foregoing definition in mind, reference throughout the specification and claims shall be made to filtration membranes and affinity membranes.

As noted hereinabove, the present invention provides non-fouling affinity polymer membranes which can be modified to bind a variety of specific proteins or other biological materials. Heretofore, it has not been readily possible to filter and concentrate proteins using a polysulfone membrane because the protein binds to the membrane, plugging the pores. As noted hereinabove, the membranes of the present invention are based upon a precursor membrane comprising a matrix polymer that is blended with a compatible copolymer. The matrix polymer is a polysulfone, or polyethersulfone, well known commercially available membrane materials having high glass transition temperatures, mechanical strength and chemical resistance. The term polysulfone shall be used herein to connote both the polysulfones and the polyethersulfones unless otherwise specified.

A good discussion of the polysulfones is presented in U.S. Pat. No. 4,230,463, the subject matter of which is incorporated herein by reference. There, it is noted that the polysulfones having aromatic hydrocarbyl-containing moieties in general possess good thermal stability, are resistant to chemical attack, and have an excellent combination of toughness and flexibility. Useful polysulfones are sold under the trade name UDEL by Union Carbide. Other useful polysulfones are sold under the trade name "ASTREL 360 Plastic" by the 3M Company. Poly(arylene ether) sulfones are also advantageous. Polyethersulfones, available from ICI Ltd., Great Britain, are also useful. Other useful polyethersulfones are sold under the trade names "P-1700" and P-3500" by Union Carbide. Still other useful polysulfones could be prepared through polymer modifications, for example, by crosslinking, grafting, quaternization and the like.

Although very few polymers are known to form compatible blends with polysulfone, the polyethers recently have been successfully employed in the present invention to modify the polysulfone matrix. The resulting membrane is hydrophilic and yet is highly resistant to leaching of the polyethers, e.g., only 1-2 ppm.

Polyethers are low molecular weight block copolymer surfactants consisting of polyethylene oxide (PEO) which is hydrophilic and polypropylene oxide (PPO) which is hydrophobic. As homopolymers, both are compatible with polysulfone although polyethylene oxide is water soluble while polypropylene oxide is water insoluble.

Concentration ranges of the polysulfone component in the membrane are typically from about 85 to 30 percent by weight, with 50 percent being preferred and for the copolymer, from about 15 to 70 percent by weight with 50 percent being preferred. Both polymer components are prepared in a water miscible solvent such as N-methylpyrrolidone (NMP), dimethylformamide (DMF), dimethylacetamide and the like.

The membrane is prepared by dissolving the block copolymer and polysulfone in one of the foregoing solvents. The solution contains from about 10 to about 25 parts by weight and from about five to about 25 parts by weight of block copolymer with 85 to 50 parts by weight of solvent to total 100 parts of solution. It is stirred at a temperature of from about 60° to 80° C. for 24-48 hours at the end of which time an optically clear one phase solution should be obtained indicating compatibility. Block copolymers having too low a cloud point temperature, e.g., 0° C. or too high a molecular weight, e.g., greater than 20,000, may lead to incompatibility with the polysulfone matrix and should theretofore be avoided. A complete discussion of the preparation and use of such ultrafiltration membranes is presented in co-pending application, Ser. No. 123,818, owned by the Assignee of record herein and the subject matter of which is incorporated by reference. These membranes are employed as a precursor membrane in the preparation of the affinity membrane.

When filtration membranes comprising polysulfone or polyethersulfone and the foregoing block copolymers are cast and then quenched in a water bath, the polyethylene oxide end of the block blooms to the membrane surface to provide a non-fouling layer which is anchored into the base polymer via the polypropylene oxide end. By using the hydroxy group on the end of the polyethylene oxide chain as a reaction site for activation of the membrane for specific protein binding, an affinity membrane is obtained which presents a surface having non-binding properties except where it has been modified to bind a specific protein or other biological molecule.

While the filtration membranes provided in the aforementioned copending application are non-fouling, the affinity membranes of this invention are intended to bind one of many different proteins or other biological molecules on their surface. The ability of the affinity membrane to function in this manner is based upon the accessibility of the hydroxy groups on the surface of the foregoing filtration membrane.

Inasmuch as there is complete coverage of the membrane surface by the several thousand molecular weight PEO block, only a limited number of hydroxy groups are present on the surface. Because it is an objective of the invention to be able to bind large immunoglobulin proteins, it is advantageous to have fewer binding sites than might be available on a known membrane of regenerated cellulose or polyvinyl alcohol.

The present invention provides two processes for the preparation of such affinity membranes. First, pendant hydroxy groups from the filtration precursor membrane can be activated by a variety of conventional chemistries followed by binding of the desired species. A second process is to perform the activation reaction on the PEO-PPO block copolymer and then use that material or a blend of that material and the original block copolymer, with the polymer matrix, to form the new membrane. An advantage of the latter method is the ability to vary the ratio of activated to unreactive block copolymer in the casting dope allowing precise control of the quantity of reactive groups, and hence the ultimate amount of bound biomaterial, on the membrane surface. Generally, the ratio can vary from about 1:100 to 50:50, activated to unactivated block copolymer, with 25:75 being preferred.

For the practice of the first process, a polysulfone/polyblend or polyethersulfone/polyblend membrane, as a precursor membrane, must first be activated. Those skilled in the art will appreciate that a variety of reactions exist for the substitution of organic constituents for pendant hydroxyl groups. For a thorough treatise reference can be made to the text *Affinity Chromatography* ed. P. D. G. Dean, W. S. Johnson and F. A. Middle (1985), the subject matter of which is incorporated herein by reference.

For the practice of the second process, the block copolymer is itself first activated, or derivatized using any available technique for the reaction of a hydroxyl group to provide a desired adduct. A solution of the derivatized block copolymer, in a water miscible solvent such as NMP, DMF or the like is mixed with a quantity of underivatized block polymer and the polymer matrix material, in the same manner as described in conjunction with the preparation of ultrafiltration membranes provided in co-pending application Ser. No. 123,818 to form, in this instance, the affinity membrane of the present invention.

Activations for both processes are conducted in the presence of an aprotic solvent such as acetonitrile which does not dissolve the membrane and known activating compounds such as sodium hydroxide, sodium borohydride, pyridine, tin tetrachloride, and the like in the presence of coupling agents such as carbodiimides. Activation can be facilitated by immersion in the solvent, activator and coupling agent compounds for several hours. For the first process, the activated polyether is recovered, the polymer matrix is then added, following which the membrane is cast as described in Ser. No. 123,818.

Several exemplary activation chemistries are provided in Table I hereinbelow. It is to be understood that the present invention is not limited to these but is rather, extendable to any reaction based on hydroxy groups or on groups that can be synthesized from hydroxy groups. In the table, the polyethylene oxide polymer has been designated by a wavy line with one hydroxyl group appended therefrom.

TABLE I

Activation Chemistries for Polyblend Membranes

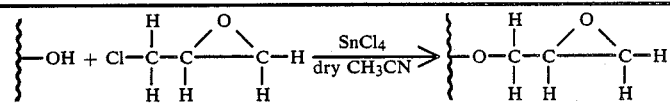

The activated or affinity membranes of activation Schemes I, II, IIIa or IIIb can be employed in a filtration process of fluids containing various biological materials that will bind to the reactive sites. Typical biological materials include proteins, peptides, hormones, antigens, antibodies, cyclodextrans, monoclonal antibodies, co-factors, substrates, enzymes, inhibitors, inactivators and the like.

Once bound, the materials can be removed from the membrane in a variety of manners known to those skilled in the art, such as pH adjustment and washing. Depending on the reactivity of the group, before as well as after removal of the biological material, the affinity membrane can be stored for variable and generally long periods of time.

GENERAL MEMBRANE PREPARATION

In order to demonstrate the preparation and properties of membranes according to the present invention, a precursor membrane was formed as follows.

The polymer blend solutions were prepared by dissolving 20 wt% of block copolymer (Pluronic Series, BASF) together with 20 wt% of polyethersulfone (Victrex 4100G, ICI Americas) in a solvent such as N-methylpyrrolidone (NMP) or dimethylformamide (DMF). An optically clear one phase solution was obtained after stirring at a temperature of 60° C. for 24-48 hours indicating that the polymer blend was compatible. The polymer blend solution was then vacuum filtered through a 40-60 frit filter. After the bubbles in the filtrate subsided the polymer solution was cast in a uniform motion at a predetermined thickness (7 to 15 mil) using a doctor knife onto either a glass, Teflon® or duPont Tyvek® #1085 substrate. The cast solution was then quenched by immersion in a 5° C. water bath (3-gallon, 12 l, bath) in one swift continuous motion. The phase inversion occurs in this step when water, which is miscible with the solvent but is a non-solvent for the polymer precipitates and initiates membrane formation.

EXAMPLES NO. 1 AND 2

To prepare an affinity membrane by the first process of the present invention and according to Scheme I, a solution of Pluronic F87 PPO-PEO block copolymer (50 percent PPO, 50 percent PEO, M.W. 7900) with free hydroxyl groups was derivatized by tin tetrachloride and epichlorohydrin according to the method of Pitha et al, Eur. J. Bioch., 94, 11-18 (1979).

The resulting block copolymer with glycidyl ether adducts was blended with non-derivatized Pluronic F87, added to a polyethersulfone solution (25% in DMF) and cast on a glass plate. The resulting film was immediately submerged in 5° C. water to form the membrane (Example No. 1) which was stored dry at room temperature. When ready for use, the membrane was re-wet with water and soaked in a solution of an amine-containing ligand for 24 hours and then rinsed repeatedly with deionized water.

A similar membrane was cast as a control (Example No. 2) without using a derivatized block copolymer. Both membranes were employed subsequently in protein adsorption studies, the results of which have been presented in Table II hereinbelow.

The second process is illustrated in the remaining examples. The precursor membrane was formed first from polyethersulfone and block copolymers of PPO-PEO, viz., Pluronic F87 and Pluronic F127 (30 percent PPO, 70 percent PEO, M.W. 12,700). Derivatization of the free hydroxyl groups from the membrane surface followed.

EXAMPLES NO. 3 AND 4

To prepare an affinity membrane according to Scheme II, four strips of the precursor membrane (2 cm×6 cm) were submerged in 100 ml of 0.1M NaOH with 0.4 gm $NaBH_4$ and 1.5 g of Araldite RD-2, a diglycidyl ether. The membranes were soaked for 16 hours in a container which was up-ended once per hour to mix the materials. One of the treated membranes, Example No. 3, and a sample of the precursor membrane, Example No. 4 (which was exposed to the same solution as Example No. 3 except for the absence of the RD-2) were soaked in 500 mg percent bovine albumin, pH 7 in phosphate buffer for two hours. The albumin samples were sent for surface protein analysis and the results are reported as Examples No. 3 and 4 in Table II.

EXAMPLES NO. 5-8

To prepare affinity membranes according to Schemes IIIa-b, four samples of the precursor membrane were rinsed with dry acetonitrile and placed in a round bottom flask with 140 ml of dry acetonitrile, 40 ml of iwhich was vacuum distilled in order to remove any residual water. Next, 5 g of succinic anhydride and 1 ml of pyridine were added to the solution which was allowed to sit overnight.

Two of the four samples were left in the mixture for another night. The remaining two samples were treated as follows. Example No. 5 was placed in pH 7 phosphate buffer with 100 mg of the coupling agent EDAC (1-ethyl-3-(3-dimethylaminopropyl)carbodiimide). The second sample, Examiner No. 7, was placed in the same mixture with micrograms of alkaline phosphatase enzyme added. After sitting in the solutions for twenty-two hours, both membranes were rinsed three times in deionized water, dried at 50° C. in a forced draft oven, sent for analysis, and reported as Examples No. 5 and 7 in Table II.

Two of the samples left in the original mixture of acetonitrile, succinic anhydride, and pyridine were removed, rinsed in acetonitrile, and placed in 100 ml solution of acetonitrile with 0.1M N-hydroxy succinimide and 0.1M EDAC. After stirring for two hours, the samples were rinsed in deionized water, one was dried as before (Example No. 6) and the other, Example No. 8 was exposed to the same alkaline phosphatase mixture as Example No. 7 above for twenty-two hours. Example No. 8 was also dried as before and Examples No. 6 and 8 sent for analysis. Results are reported in Table II.

Thus, it can be seen that for activation Scheme I, epichlorohydrin has been reacted with the hydroxyl to provide a glycidyl ether adduct pendant from the polyethylene oxide block and subsequently, the membrane. In Scheme II, 1,4-butanediol diglycidoxy ether has been reacted with the hydroxyl to provide a glycidyl ether adduct further away from the membrane. In Scheme IIIa, succinic anhydride has been reacted with the hydroxyl to provide a dicarboxylate group pendant from the membrane. In Scheme IIIb, the activated membrane of IIIa is further reacted with N-hydroxy succinimide to provide the imide modified carboxylate group.

Protein binding studies were conducted with bovine serum albumin (BSA, Sigmon Chemicals) or alkaline phosphatase (A.P.). Each of the membranes from the foregoing examples was rinsed several times with water and then Examples No. 1-4 were exposed for four hours to 500 mg% BSA in pH 7 buffer while Examples No. 5-8 were exposed to 200 micrograms of alkaline phosphatase in pH 7.0 buffer for 22 hours.

TABLE II

Affinity Activation of Precursor Polyblend Membranes

| Scheme | Ex. No. | Protein | Amount Bound |
|---|---|---|---|
| I | 1 | BSA | 2 $\mu g/cm^2$ |
| I(Blank) | 2 | BSA | 0.5 $\mu g/cm^2$ |
| II | 3 | BSA | 5.0 $\mu g/cm^2$ |
| II(Blank) | 4 | BSA | 0.2 $\mu g/cm^2$ |
| IIIa | 5 | A.P. | ND at 0.1 Units/cm$^2$ |
| IIIb | 6 | A.P. | ND at 0.1 Units/cm$^2$ |

TABLE II-continued

Affinity Activation of Precursor Polyblend Membranes

| Scheme | Ex. No. | Protein | Amount Bound |
|---|---|---|---|
| IIIa (EDAC) | 7 | A.P. | 0.5 Units: 8 μg/cm$^2$ |
| IIIb (EDAC) | 8 | A.P. | 0.3 Units: 5 μg/cm$^2$ |

With reference to Examples No. 1 and 2 in Table II, it is notable that four times the amount of protein was bound by the affinity membrane than the precursor. In Examples No. 3 and 4, were the glycidyl ether adduct was further removed from the membrane surface, the difference in protein binding was 25 times greater between the affinity membrane and the precursor.

With respect to Scheme III, analysis for alkaline phosphatase showed none detected (ND) for membranes IIIa and IIIb. However, in the presence of EDAC, either membrane IIIa or IIIb will bind alkaline phosphatase although membrane IIIb appeared to be more efficient.

Thus, it should be evident that the affinity membranes of this invention can be employed to remove one or more of the foregoing biological materials from a fluid by selection of a specific adduct for the membrane that will bind the desired protein or other material. In addition to this process for selective binding, the present invention provides another process of use employing a further modified affinity membrane.

This second process employs an affinity membrane of the present invention which has bound a first type of biological material, which is itself a ligand for a second type of biological material. For instance, no convenient adduct may be available to bind a particular antibody, but only the corresponding antigen. After the antigen has been bound to the membrane a further modified affinity membrane is available which will bind the antibody.

Other examples include, the converse situation of binding the antibody first to the membrane which is then employed to capture the corresponding antigen. Either technique as well as one involving the use of monoclonal antibodies would have utility in the development of cures to diseases or the filtration of blood to detect and remove antibodies for AIDS, as an example. Enzymes can be employed to remove carbohydrates, proteins, hormones and the like and vice-versa. Wine treatment can be conducted in this manner to remove only the enzymes responsible for discoloration upon standing.

As should be appreciated by those skilled in the art, the potential applications are exceedingly great. The affinity membrane carrying substantially any first type of biological material can be employed to detect bind or remove a corresponding second type of biological material from a fluid.

Based upon the foregoing disclosure it should be readily apparent that the affinity membranes of the present invention are binding to specific substances and that they can be readily obtained by activating the hydroxyl groups pendant from the surface of a precursor membrane. It should also be evident that the affinity membranes of this invention can be varied by composition as well as by specific biological materials that can be bound thereto for additional affinity separations.

In like fashion, it is to be understood that the affinity membranes of this invention can be employed in a variety of applications where protein substances or other biological materials must be filtered. Inasmuch as all of these processes can be practiced in a variety of membrane apparatus including artificial kidneys as well as other types of dialysis units, units such as the Amicon cell discussed herein, hollow fiber units, counter-current flow units and the like, it is to be understood that practice of the present invention is not to be limited to any specific form of apparatus.

In conclusion, the examples set forth herein are merely illustrative of certain properties and are not to be construed as limiting practice of the invention. Nor, should the invention be limited to the specific process of binding bovine serum albumin or alkaline phosphatase. It is to be understood that any variations evident fall within the scope of the claimed invention; therefore, the selection of specific component members or ingredients can be determined without departing from the spirit of the invention herein disclosed and described. Moreover, the scope of the invention shall include all modifications and variations that may fall within the scope of the attached claims.

I claim:

1. A polymeric affinity membrane comprising:
   a structure for binding a preselected biological material consisting essentially of a hydrophilic precursor filtration membrane comprising a water-insoluble polymer matrix and a matrix-compatible copolymer; and
   a plurality of reaction sites provided on the surface of said membrane selective to bind a specific biological material, said reaction sites being selected from the group consisting of organic adducts synthesized from hydroxyl groups supplied by said matrix-compatible copolymer.

2. A polymeric affinity membrane, as set forth in claim 1, wherein said water insoluble polymer matrix is selected from the group consisting of polysulfones and polyethersulfones.

3. A polymeric affinity membrane, as set forth in claim 1, wherein said matrix compatible copolymer comprises from about 40 to 90 percent by weight of polyethylene oxide and from about 60 to 10 percent by weight polypropylene oxide.

4. A polymeric affinity membrane, as set forth in claim 1, comprising from about 85 to 30 parts by weight of said polymer matrix and from about 15 to 70 parts by weight of said copolymer.

5. A polymeric affinity membrane, as set forth in claim 1, further comprising at least one type of biological material bound to said reaction sites and having an affinity for a different biological material.

6. A polymeric material affinity membrane, as set forth in claim 5, wherein said biological materials are selected from the group consisting of proteins, peptides, hormones, antigens, antibodies, monoclonal antibodies, cyclodextrans, co-factors, substrates, enzymes, inhibitors and inactivators.

* * * * *